(12) United States Patent  
Chiang et al.

(10) Patent No.: US 9,380,957 B2
(45) Date of Patent: Jul. 5, 2016

(54) MEASUREMENT DEVICE WITH ELECTROENCEPHALOGRAPHY AND ELECTROCARDIOGRAPHY FUNCTIONALITIES

(71) Applicant: Wistron Corporation, New Taipei (TW)

(72) Inventors: Chi-Chan Chiang, New Taipei (TW); Chia-Yuan Wang, New Taipei (TW); Chia-Liang Lai, New Taipei (TW); Ting-Wen Liu, New Taipei (TW); Chun-Chih Lai, New Taipei (TW)

(73) Assignee: Wistron Corporation, Hsichih, New Taipei (TW)

( * ) Notice: Subject to any disclaimer, the term of this patent is extended or adjusted under 35 U.S.C. 154(b) by 0 days.

(21) Appl. No.: 14/964,582

(22) Filed: Dec. 10, 2015

(65) Prior Publication Data

US 2016/0089034 A1 Mar. 31, 2016

Related U.S. Application Data

(62) Division of application No. 14/177,237, filed on Feb. 11, 2014, now Pat. No. 9,282,912.

(30) Foreign Application Priority Data

Sep. 13, 2013 (TW) .............................. 102133252 A

(51) Int. Cl.
*A61B 5/0408* (2006.01)
*A61B 5/0478* (2006.01)
*A61B 5/00* (2006.01)
*A61B 5/04* (2006.01)

(52) U.S. Cl.
CPC ............. *A61B 5/0478* (2013.01); *A61B 5/0006* (2013.01); *A61B 5/04012* (2013.01); *A61B 5/04085* (2013.01)

(58) Field of Classification Search
CPC ............. A61B 5/0404; A61B 5/04085; A61B 5/0478; A61B 5/6814; A61B 5/6825; A61B 5/6826; A61B 2560/0425; A61B 2560/0468
USPC .................................................. 600/383, 393
See application file for complete search history.

(56) References Cited

U.S. PATENT DOCUMENTS

| 8,965,492 | B2* | 2/2015 | Baker | A61B 5/0006 600/372 |
| 2003/0088167 | A1* | 5/2003 | Fendrock | A61B 5/0408 600/372 |
| 2009/0124869 | A1* | 5/2009 | Hu | A61B 5/0476 600/301 |

\* cited by examiner

*Primary Examiner* — Lee S Cohen
(74) *Attorney, Agent, or Firm* — Winston Hsu; Scott Margo

(57) ABSTRACT

A measurement device with electroencephalography (EEG) and electrocardiography (ECG) functionalities includes a shell and a turning structure. The shell includes a first contact and a second contact located at a first side of the shell; and a third contact. The turning structure, disposed on the shell, is utilized for adjusting the third contact to be located at the first side when the measurement device is in an EEG mode, and adjusting the third contact to be located at a second side of the shell when the measurement device is in an ECG mode, wherein the second side is substantially opposite to the first side.

4 Claims, 8 Drawing Sheets

MEASUREMENT DEVICE WITH ELECTROENCEPHALOGRAPHY AND ELECTROCARDIOGRAPHY FUNCTIONALITIES

CROSS REFERENCE TO RELATED APPLICATIONS

This application is a divisional of application Ser. No. 14/177,237, filed on Feb. 11, 2014, now U.S. Pat. No. 9,282,912, and entitled "MEASUREMENT DEVICE WITH ELECTROENCEPHALOGRAPHY AND ELECTROCARDIOGRAPHY FUNCTIONALITIES", the contents of which are incorporated herein in their entirety.

BACKGROUND OF THE INVENTION

1. Field of the Invention

The present invention relates to a measurement device, and more particularly, to a measurement device capable of electroencephalography and electrocardiography functionalities.

2. Description of the Prior Art

The electroencephalography (EEG) is utilized for measuring brainwave signals. The EEG can amplify weak physiological signals generated in the human brain, and perform analysis and comparison on these signals; hence, the EEG is typically used for brain disease diagnosis or sleep quality monitoring. The electrocardiography (ECG) is a detection system for recording cardiac signals. The ECG can capture and record cardiac signals via electronic signals on the skin. In each heartbeat, polarization of cardiac cells may generate slight voltage variations at the surface of the skin; the ECG can record such variations, in order to assist with diagnosis of heart disease.

Modern EEG and ECG are measurement products with mono-functionality, i.e. there is no bio-electronic product which can integrate both EEG and ECG functionalities. If the EEG and ECG functionalities could be effectively integrated in a single device, the facility and usage of these products could be significantly enhanced.

Thus, there is a need to provide a measurement device integrating EEG and ECG functionalities. Related production costs could be reduced by modifying internal operation circuits and external designs of signal contacts, to effectively minimize the size of the products as well as create additional features. The range of application of this product would therefore be increased, which could help in reducing related healthcare costs.

SUMMARY OF THE INVENTION

It is therefore an objective of the present invention to provide a measurement device having both electroencephalography (EEG) and electrocardiography (ECG) functionalities, which is capable of receiving EEG signals and monitoring sleep quality in an EEG mode and receiving ECG signals in an ECG mode. Such a measurement device may also transmit the received signals to medical centers for subsequent analysis and processing.

The present invention discloses a measurement device with EEG and ECG functionalities. The measurement device comprises a shell and a turning structure. The shell comprises a first contact and a second contact located at a first side of the shell; and a third contact. The turning structure, disposed on the shell, is utilized for adjusting the third contact to be located at the first side when the measurement device is in an EEG mode, and adjusting the third contact to be located at a second side of the shell when the measurement device is in an ECG mode, wherein the second side is substantially opposite to the first side.

The present invention further discloses a measurement device with EEG and ECG functionalities. The measurement device comprises a shell, an operation circuit and a switching device. The shell comprises a first contact and a second contact located at a first side of the shell; a third contact, located at the first side of the shell; and a fourth contact, located at a second side of the shell, wherein the second side is substantially opposite to the first side. The operation circuit is disposed in the shell. The switching device, coupled to the operation circuit, is utilized for connecting the third contact with the operation circuit and disconnecting the fourth contact from the operation circuit when the measurement device is in an EEG mode, and connecting the fourth contact with the operation circuit and disconnecting the third contact from the operation circuit when the measurement device is in an ECG mode.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
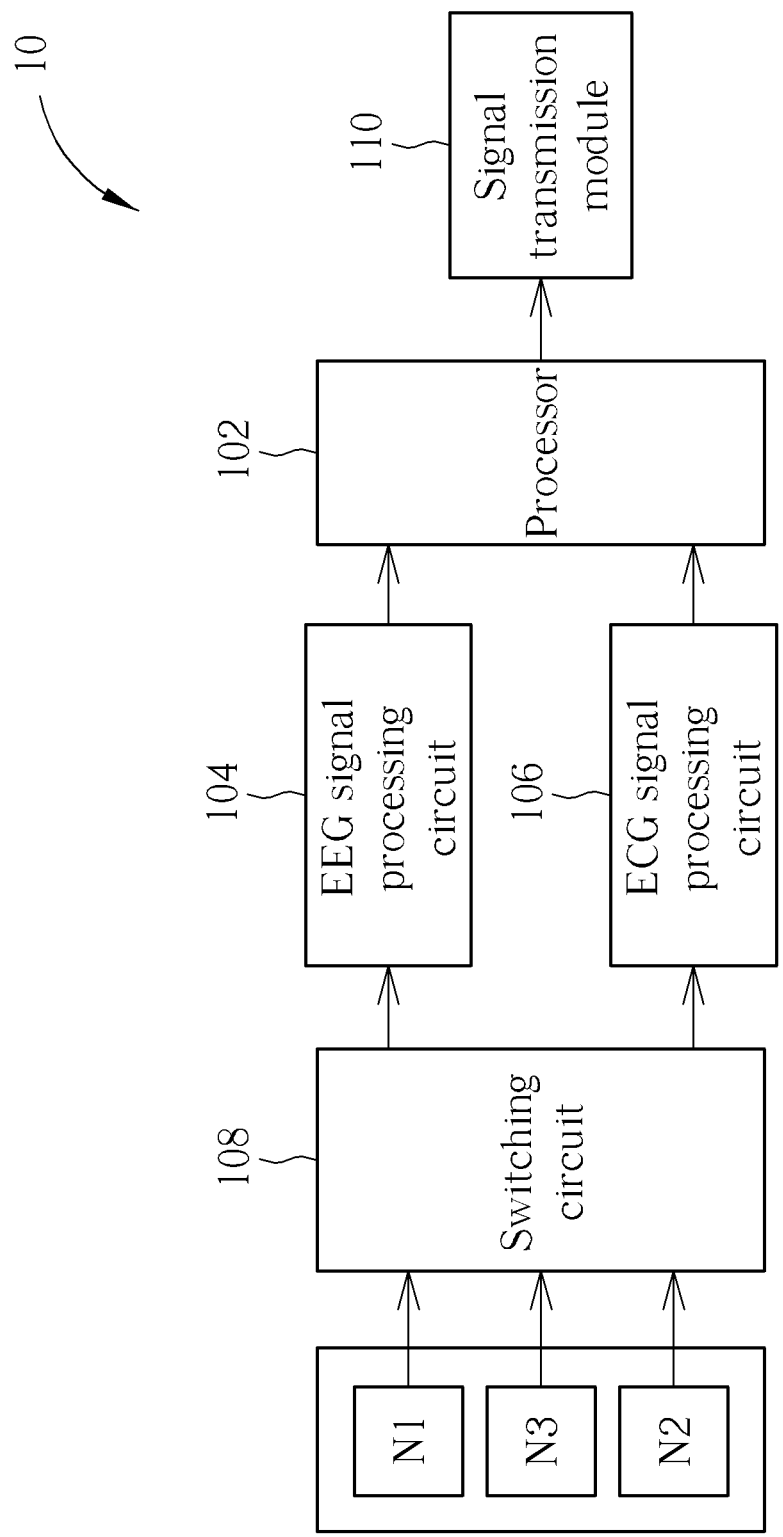
FIG. 1 is a schematic diagram of a circuit structure of a measurement device according to an embodiment of the present invention.

Please refer to FIG. 1, which is a schematic diagram of a circuit structure of a measurement device 10 according to an embodiment of the present invention. As shown in FIG. 1, the measurement device includes contacts N1-N3, a processor 102, an electroencephalography (EEG) signal processing circuit 104, an electrocardiography (ECG) signal processing circuit 106, a switching circuit 108 and a signal transmission module 110. The contacts N1-N3, located on the shell of the measurement device 10, are utilized for measuring physiological signals of a human body. When the measurement device 10 is in an EEG mode, the contacts N1-N3 may be placed on the forehead of a user, in order to perform EEG measurement and sleep management. When the measurement device 10 is in an ECG mode, the user may hold the measurement device 10 in their hand, e.g. by placing the right index finger, the left index finger and the left thumb on the contacts N1-N3, respectively, in order to perform ECG measurement.

The sensing electrodes, composed of metal, conductive foam or other electrically conductive materials, may be disposed on the contacts N1-N3. For example, when the measurement device 10 is utilized for EEG measurement, the measurement device 10 is worn on the forehead of the user; hence the conductive foam may be utilized as sensing electrodes on the contacts N1-N3, in order to increase the comfort of the user. When the measurement device 10 is utilized for ECG measurement, ergonomic materials may be applied (e.g. metal).

Please keep referring to FIG. 1. The processor 102 is utilized for performing signal processing. The EEG signal processing circuit 104, coupled to the processor 102, is utilized for amplifying and filtering the signals received in the EEG mode. The ECG signal processing circuit 106, coupled to the processor 102, is utilized for amplifying and filtering the signals received in the ECG mode. The switching circuit 108 is utilized for switching the signal path. When the measurement device 10 is in the EEG mode, the switching circuit 108 controls the contacts N1-N3 to be coupled to the EEG signal processing circuit 104. When the measurement device 10 is in the ECG mode, the switching circuit 108 controls the contacts N1-N3 to be coupled to the ECG signal processing circuit 106. The signal transmission module 110, coupled to the processor 102, is utilized for transmitting signals to an external electronic device after the signals are interpreted by the processor 102. These signals will then be transmitted to a medical center via the Internet for subsequent analysis and processing. The signal transmission module 110 may use various wireless communication technologies such as Bluetooth or Wireless Fidelity (Wi-Fi) to transmit signals. The external electronic device may be any device with signal transmission functionality such as a laptop, tablet or smart phone.

In detail, the EEG and ECG having a single measurement channel may have three signal contacts, two of which may correspond to a pair of differential signals of the single measurement channel and the other may correspond to a reference signal. There is a signal processing circuit which can operate in an EEG or an ECG mode for processing EEG signals or ECG signals, respectively. In general, the signal processing circuit is utilized for filtering and amplifying signals. Since the strength and frequency of the EEG signals and the ECG signals are different, different signal processing circuits are required for the processing procedure. As a result, the EEG signal processing circuit 104 and the ECG signal processing circuit 106 are utilized in the measurement device 10 for processing EEG signals and ECG signals, respectively. The switching circuit 108 is further utilized for performing switching according to whether the measurement device 10 is in the EEG mode or the ECG mode.

The disposition of the contacts N1-N3 may need to be switched according to the measurement mode of the measurement device 10. When the measurement device 10 is in the EEG mode, the measurement device 10 is worn on the forehead, and the contacts N1-N3 need to touch the forehead simultaneously, and therefore have to be located at the same side on the shell of the measurement device 10. When the measurement device 10 is in the ECG mode, the user holds the measurement device 10 in their hand by placing the right index finger, the left index finger and the left thumb on the contacts N1-N3, respectively. If the right index finger, the left index finger and the left thumb correspond to the contacts N1, N2 and N3 respectively, the contacts N1 and N2 have to be located at the same side on the shell of the measurement device 10, and the contact N3 has to be located at the side opposite to the contacts N1 and N2. Thus, a turning structure may be utilized for adjusting the contact N3, which allows the contact N3 to be located at the same side with the contacts N1 and N2 when the measurement device 10 is in the EEG mode, and to be located at the side opposite to the contacts N1 and N2 when the measurement device 10 is in the ECG mode.

Figure 2A:
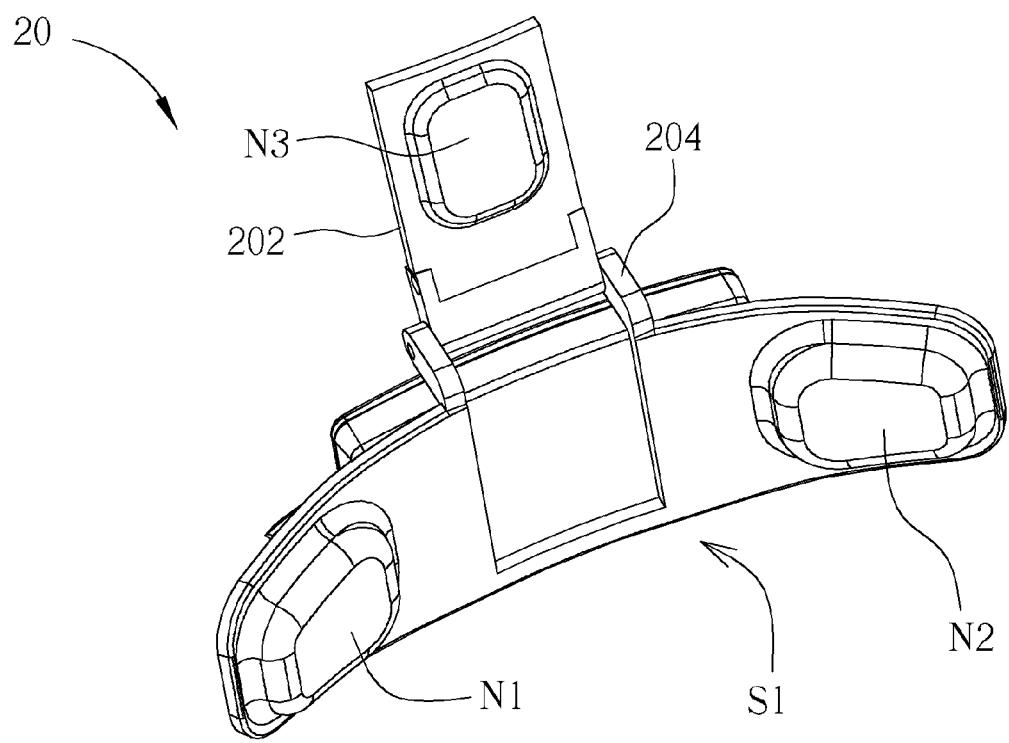
FIG. 2A and FIG. 2B are schematic diagrams of a measurement device according to another embodiment of the present invention.
Figure 2B:
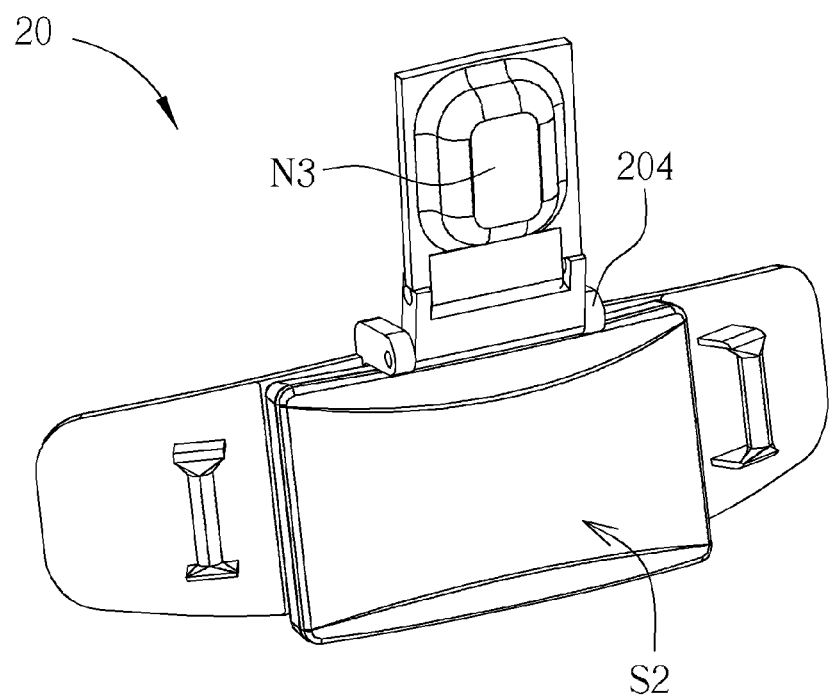

An embodiment of the turning structure is illustrated in FIG. 2A and FIG. 2B, which are schematic diagrams of a measurement device 20 according to an embodiment of the present invention. FIG. 2A and FIG. 2B respectively illustrate the appearance of the measurement device 20 from a first side S1 and a second side S2 of the shell of the measurement device 20. As shown in FIG. 2A and FIG. 2B, the measurement device 20 includes a plate 202, a pivot 204 and contacts N1-N3. The plate 202, which is connected with the shell of the measurement device 20 via the pivot 204, may be flipped between the first side S1 and the second side S2 of the shell. The contacts N1 and N2 are located at the first side S1 of the shell, and the contact N3 is located at the plate 202. When the measurement device 20 is in the EEG mode, the plate 202 may be flipped to the first side S1, so that the user may wear the measurement device 20 on the forehead to perform EEG measurement. When the measurement device 20 is in the ECG mode, the plate 202 may be flipped to the second side S2, so that the user may hold the measurement device 20 in their hand to perform ECG measurement.

Figure 3A:
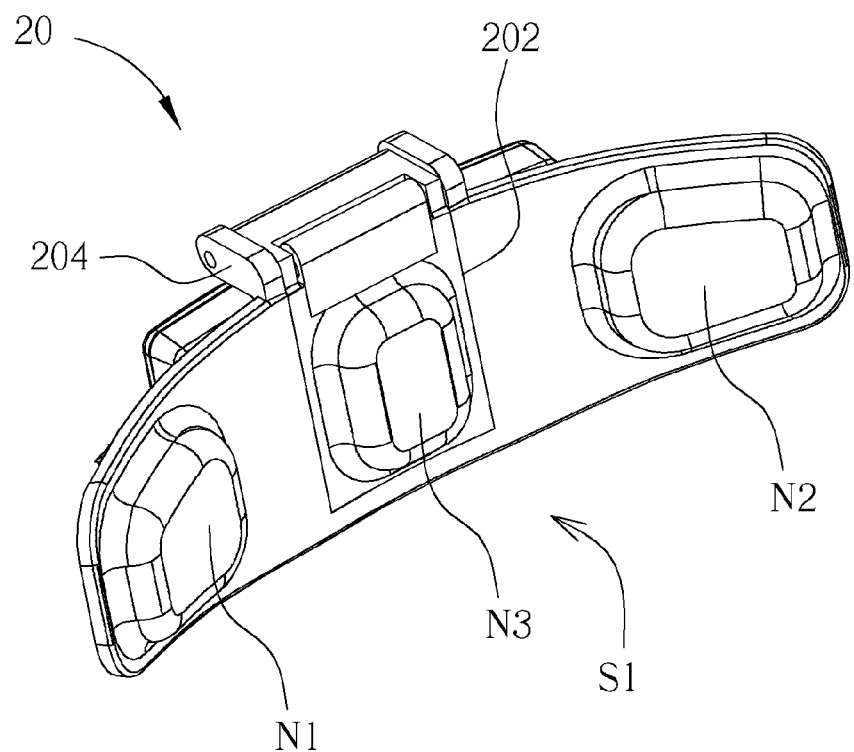
FIG. 3A and FIG. 3B are schematic diagrams of the measurement device shown in FIG. 2 in an EEG mode.
Figure 3B:
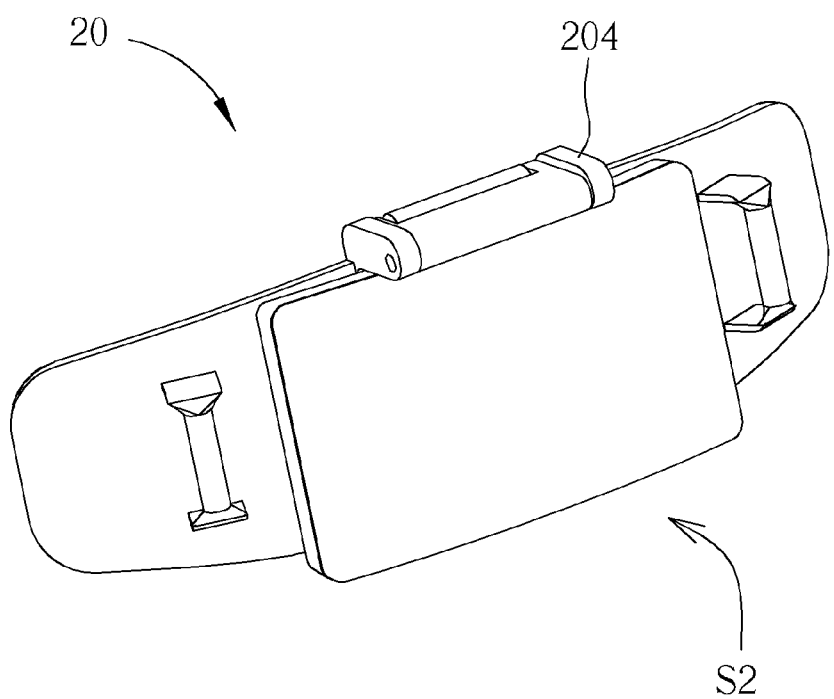

Please refer to FIG. 3A and FIG. 3B, which are schematic diagrams of the measurement device 20 in the EEG mode. FIG. 3A and FIG. 3B respectively illustrate the appearance of the measurement device 20 from the first side S1 and the second side S2 of the shell of the measurement device 20. As shown in FIG. 3A and FIG. 3B, in the EEG mode, the plate 202 is flipped to the first side S1, so that the contact N3 is turned to the first side S1 with the plate. As a result, the contacts N1-N3 are all located at the same side on the shell of the measurement device 20, enabling the user to wear the measurement device 20 on their forehead to perform EEG measurement.

Figure 4A:
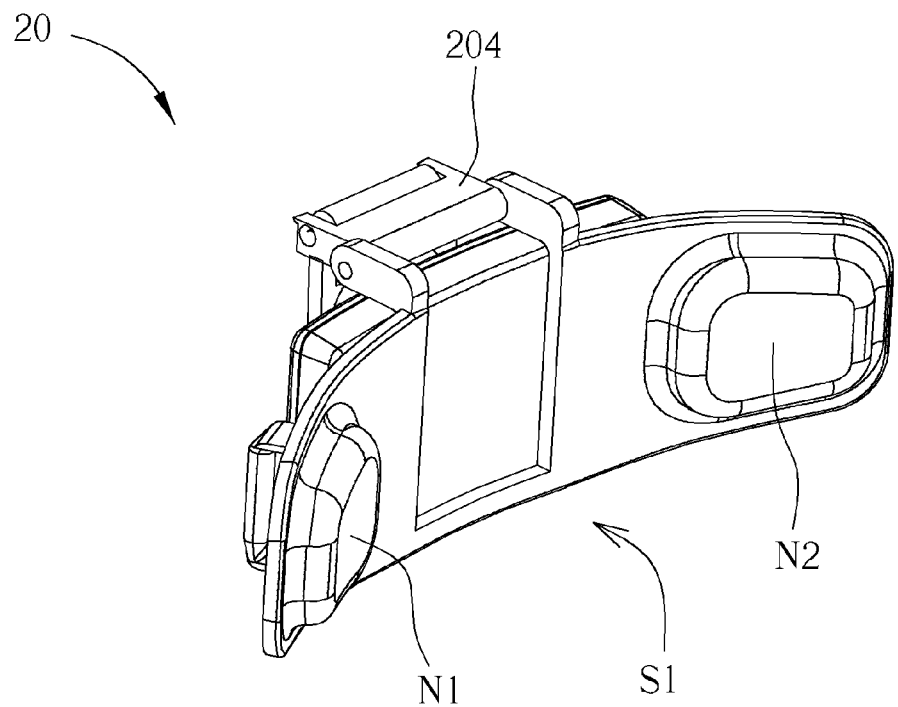
FIG. 4A and FIG. 4B are schematic diagrams of the measurement device shown in FIG. 2 in an ECG mode.
Figure 4B:
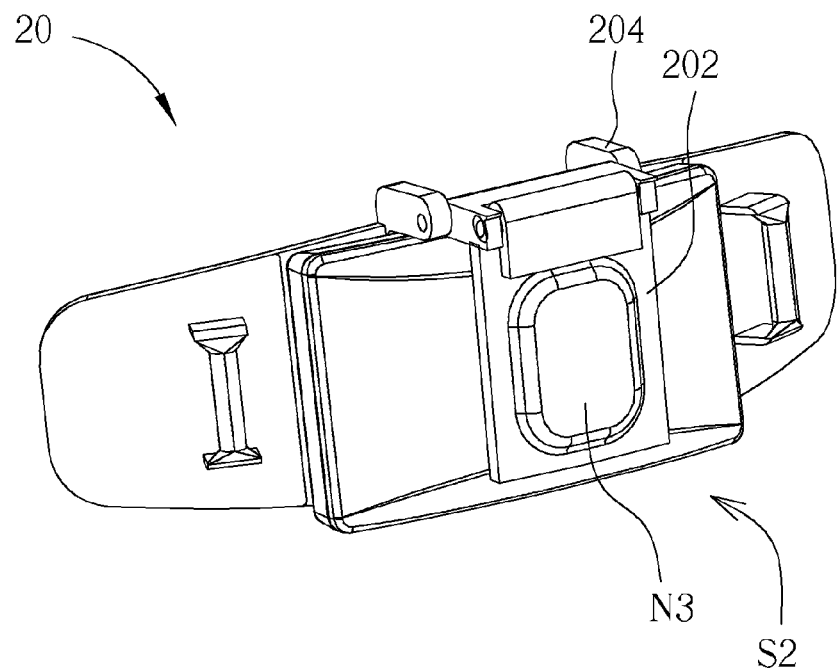

Please refer to FIG. 4A and FIG. 4B, which are schematic diagrams of the measurement device 20 in the ECG mode. FIG. 4A and FIG. 4B respectively illustrate the appearance of the measurement device 20 from the first side S1 and the second side S2 of the shell of the measurement device 20. As shown in FIG. 4A and FIG. 4B, in the ECG mode, the plate 202 is flipped to the second side S2, so that the contact N3 is turned to the second side S2 with the plate. As a result, the contact N3 and the contacts N1 and N2 are located at opposite sides on the shell of the measurement device 20, enabling the user to hold the measurement device 20 by placing both index fingers on the contacts N1 and N2 respectively and placing the left thumb on the contact N3 to perform ECG measurement.

In some embodiments, the measurement device 20 includes a detector element (e.g. a tact switch or a light sensing elements) coupled to the switching circuit 108. The detector element may automatically detect the flipping status of the measurement device 20. The switching circuit 108 can therefore automatically switch the inside operation circuits to perform corresponding signal processing according to whether the measurement device 20 is in the EEG mode or the ECG mode. As a result, the user only needs to flip the plate 202, and the system may be switched to the corresponding measurement mode accordingly. In other embodiments, the measurement device 20 may include a manual switch for manually controlling the switching circuit 108 to switch between the EEG mode and the ECG mode. In further embodiments, the abovementioned external electronic devices may also be utilized for switching the measurement device 20 between the EEG mode and the ECG mode.

Please note that the above-mentioned dispositions of the contacts and the implementations of the turning structure are only one of various embodiments according to the present invention. Those skilled in the art can make various modifications and alternations according to requirements. The purpose of adjusting the contact N3 to be located at the same side or opposite side with the contacts N1 and N2 is to allow the user to conveniently measure the physiological signals in both the EEG mode and the ECG mode. In practice, the disposition of the contacts N1-N3 may not need to be located at the same side or on exactly opposite sides. Instead, the position of the contacts N1-N3 may be adjusted ergonomically. For example, when the measurement device 10 is worn on the user's forehead for EEG measurement, the contacts N1-N3 may not be disposed at the same flat surface, and may be adjusted according to the radian or the shape of the forehead. When the measurement device 10 is held in the user's hand for ECG measurement, the contact N3 may not be disposed in the middle place on the shell, and may be disposed on the left-hand side of the user, which allows the user to easily put their left thumb on the contact N3. The turning structure may also be realized by any reversible material or structure, and is not limited to the above method with the plate 202 and the pivot 204. Moreover, the contact N3 appearing on both sides of the plate 202 may be a single conductive material, or may be two homogeneous or heterogeneous conductive materials electrically connected to each other or separately coupled to the switching circuit 108. For example, at one side, the conductive material of the contact N3 may be realized by conductive foam for greater comfort in the EEG mode; at the other side, a metal conductive film may be applied as the contact N3, which allows the user to easily press the contact N3 in the ECG mode.

Figure 5A:
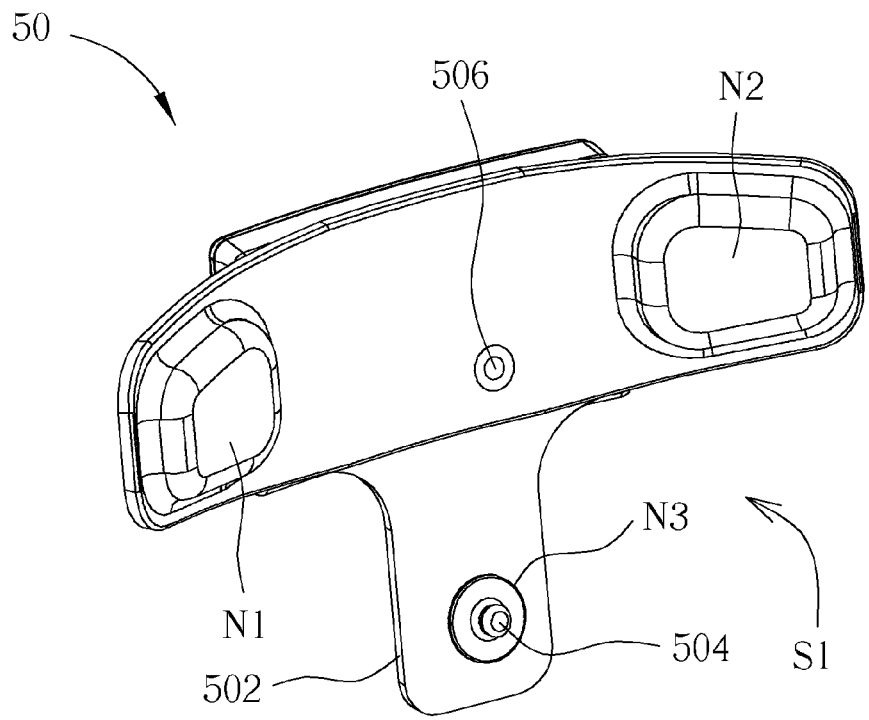
FIG. 5A and FIG. 5B are schematic diagrams of a measurement device according to another embodiment of the present invention.
Figure 5B:
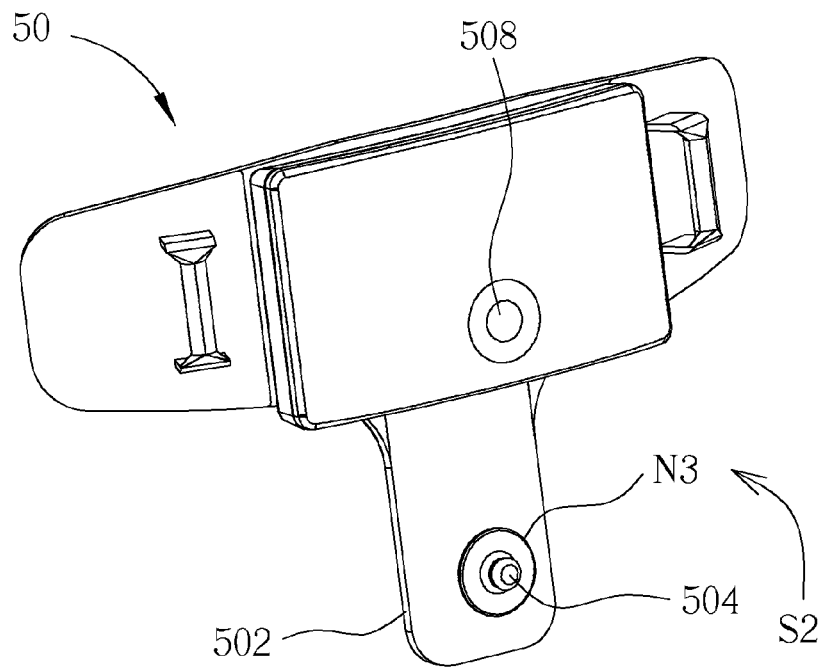

Please refer to FIG. 5A and FIG. 5B, which are schematic diagrams of a measurement device 50 according to an embodiment of the present invention. FIG. 5A and FIG. 5B respectively illustrate the appearance of the measurement device 50 from a first side S1 and a second side S2 of the shell of the measurement device 50. As shown in FIG. 5A and FIG. 5B, the measurement device 50 includes a belt 502, a button 504, button wraps 506, 508 and contacts N1-N3. A terminal of the belt 502 is connected to the shell of the measurement device 50, and the button 504 is located at the other terminal of the belt 502. The button wraps 506 and 508, respectively located at the first side S1 and the second side S2 of the shell of the measurement device 50, are utilized for fixing the belt 502. The contacts N1 and N2 are disposed at the first side S1 of the shell, and the contact N3 is disposed on the belt 502. When the measurement device 50 is in the EEG mode, the belt 502 may be turned to the first side S1 and the button 504 is fixed onto the button wrap 506 at the first side S1. At this moment, the contacts N1-N3 are all located at the first side S1, so that the user may easily wear the measurement device 50 on their forehead for EEG measurement. When the measurement device 50 is in the ECG mode, the belt 502 may be turned to the second side S2 and the button 504 is fixed onto the button wrap 508 at the second side S2, so that the contacts N1 and N2 are located at the first side S1 and the contact N3 is located at the second side S2. This enables the user to hold the measurement device 50 in their hand for ECG measurement.

As shown in FIG. 5A and FIG. 5B, the contact N3 and the button 504 are both located at the same terminal of the belt 502; thus, in some embodiments, the contact N3 may also be realized by the button 504. In other words, the button 504 and the button wraps 506 and 508 may be realized by metal materials or other conductive materials, and the button 504 or the button wraps 506 and 508 may be electrically connected to the operation circuit inside the measurement device 50. As long as the user touches the button 504, the measurement device 50 may sense the physiological signals and transmit the signals to the operation circuit for subsequent signal processing. Please note that, in other embodiments, other fixing devices or fixing methods may be utilized for fixing the belt 502 on the first side S1 or the second side S2 of the shell without using any buttons. For example, Velcro may be utilized for adhering the belt 502 to the first side S1 or the second side S2, and is not limited herein.

Figure 6:
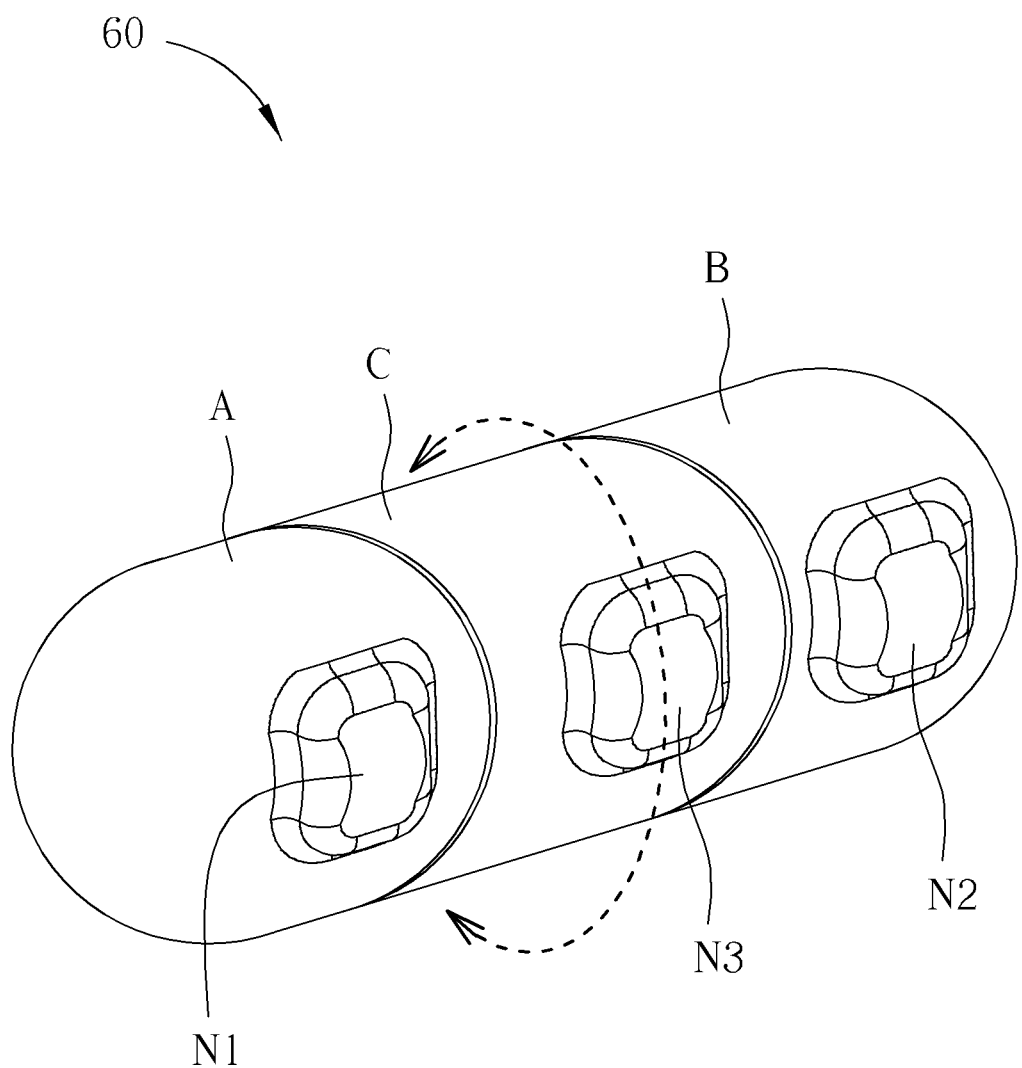
FIG. 6 is a schematic diagram of a measurement device according to another embodiment of the present invention.

Please refer to FIG. 6, which is a schematic diagram of a measurement device 60 according to an embodiment of the present invention. As shown in FIG. 6, the measurement device 60 utilizes another method to realize the turning structure. The shell of the measurement device 60 is divided into three parts A, B and C, and the contacts N1, N2 and N3 are located at A, B and C, respectively. C is embedded between A and B in a reversible manner. When the measurement device 60 is in the EEG mode, C may be turned to adjust the contacts N1, N2 and N3 so that they are located at the same side of the shell. This enables the user to wear the measurement device 60 on their forehead for EEG measurement. When the measurement device 60 is in the ECG mode, C may be turned to adjust the contact N3 to be located at the side opposite to the contacts N1 and N2. This enables the user to hold the measurement device 60 for ECG measurement.

Figure 7A:
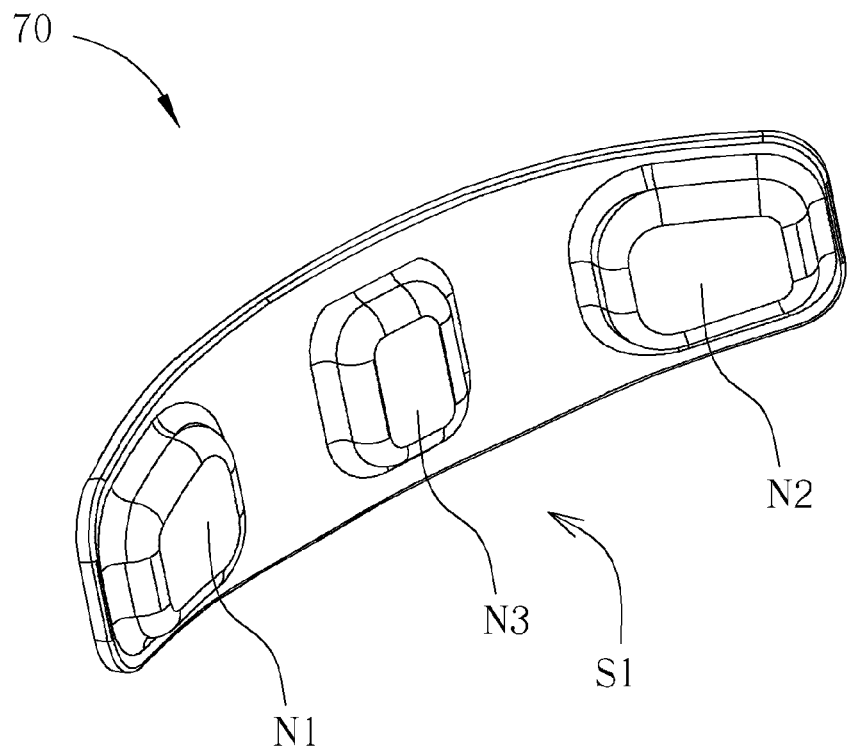
FIG. 7A and FIG. 7B are schematic diagrams of a measurement device according to another embodiment of the present invention.
Figure 7B:
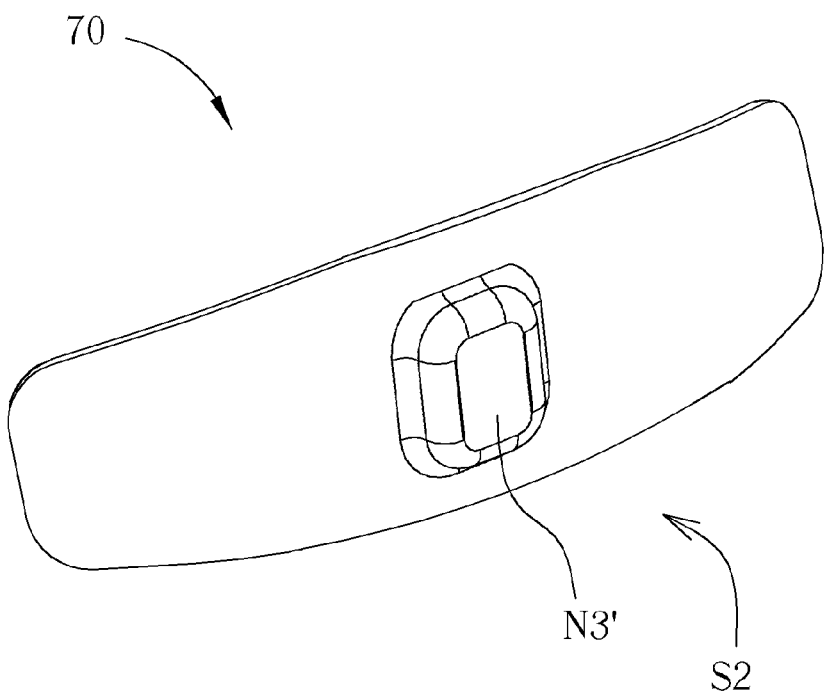

In some embodiments, switching between the EEG mode and the ECG mode may be performed without the turning structure. Please refer to FIG. 7A and FIG. 7B, which are schematic diagrams of a measurement device 70 according to an embodiment of the present invention. FIG. 7A and FIG. 7B respectively illustrate the appearance of the measurement device 70 from a first side S1 and a second side S2 of the shell of the measurement device 70. As shown in FIG. 7A and FIG. 7B, the measurement device 70 does not need to be reversed. Instead, three contacts N1, N2 and N3 are disposed at the first side S1 of the shell and a contact N3' is disposed at the second side S2 of the shell in the measurement device 70. A switching device is utilized inside the measurement device 70 for switching the contact N3 or N3' to be connected to the operation circuit in different measurement modes. For example, when the measurement device 70 is in the EEG mode, the switching device may connect the contact N3 with the operation circuit. When the measurement device 70 is in the ECG mode, the switching device may connect the contact N3' with the operation circuit. In the EEG mode, the contacts N1, N2 and N3 located at the same side of the shell may be connected to the operation circuit simultaneously; hence, the user may wear the measurement device 70 on their forehead for EEG measurement. In the ECG mode, the contacts N1 and N2 located at the first side S1 of the shell and the contact N3' located at the second side S2 of the shell may be connected to the operation circuit simultaneously; hence, the user may hold the measurement device 70 in their hand for ECG measurement.

Figure 8:
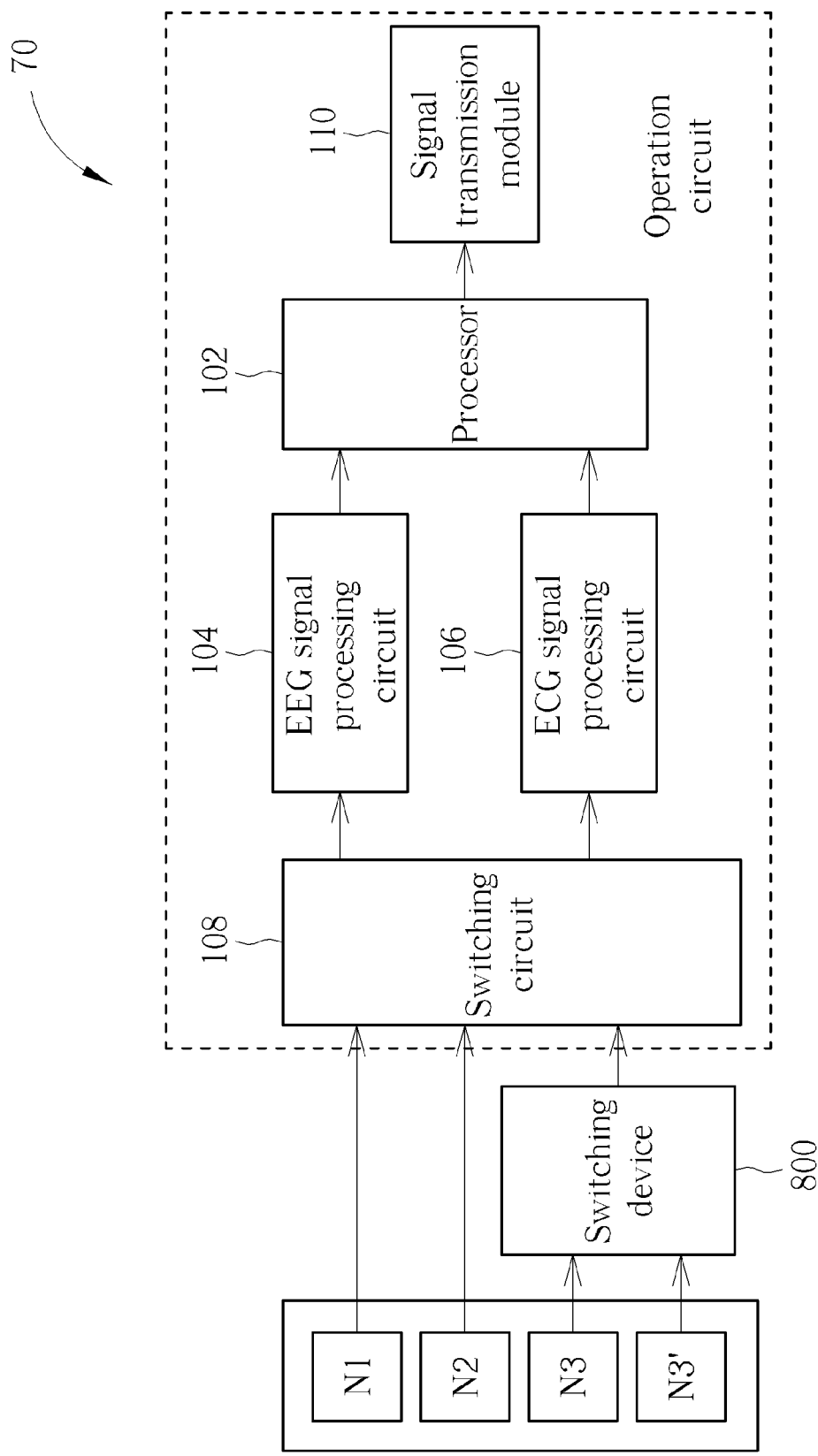
FIG. 8 is a schematic diagram of a detailed circuit structure of the measurement device shown in FIGS. 7A and 7B.

Please refer to FIG. 8, which is a schematic diagram of a detailed circuit structure of the measurement device 70. As shown in FIG. 8, the circuit structure of the measurement device 70 is similar to that of the measurement device 10 shown in FIG. 1, so the components with similar functions are denoted by the same symbols. The main difference between the measurement device 70 and the measurement device 10 is that the measurement device 70 further includes a contact N3' and a switching device 800. In addition, the operation circuit is specified in FIG. 8. The switching device 800 is used for switching between the contacts N3 and N3', while the switching circuit 108 is used for switching between the EEG signal processing circuit 104 and the ECG signal processing circuit 106. Those skilled in the art should know that the switching device 800 may be implemented by any type of switch with circuit design techniques.

In some embodiments, when the measurement device 70 is in the EEG mode, access between the contact N3' and the operation circuit may be disconnected, in order to prevent unnecessary noise from being received via the contact N3'. Similarly, when the measurement device 70 is in the ECG mode, access between the contact N3 and the operation circuit may also be disconnected, in order to prevent unnecessary noise from being received via the contact N3. In addition, a lid may be disposed on the surface of the contact N3 or the contact N3'. The lid may cover the contact when the contact is not utilized, in order to prevent the contact from receiving unnecessary noise or being damaged. For example, when the measurement device 70 is in the EEG mode, the lid on the contact N3 may be open and the lid on the contact N3' may be closed. When the measurement device 70 is in the ECG mode, the lid on the contact N3' may be open and the lid on the contact N3 may be closed.

In the prior art, the EEG and ECG are measurement products with mono-functionality, such that there is no bio-electronic product that can integrate both EEG and ECG functionalities. In contrast, the measurement device of the present invention can effectively integrate the functionalities of EEG and ECG by modifying internal operation circuits and external designs of signal contacts. This achieves the benefits of minimizing the size of the products, thereby increasing the willingness of a user to use the products, which could result in reducing healthcare costs.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A measurement device with electroencephalography (EEG) and electrocardiography (ECG) functionalities, comprising:

a shell, comprising:

a first contact and a second contact located at a first side of the shell;

a third contact, located at the first side of the shell; and a fourth contact, located at a second side of the shell, wherein the second side is substantially opposite to the first side;

an operation circuit, disposed in the shell; and a switching device, coupled to the operation circuit, for connecting the third contact with the operation circuit and disconnecting the fourth contact from the operation circuit when the measurement device is in an EEG mode, and connecting the fourth contact with the operation circuit and disconnecting the third contact from the operation circuit when the measurement device is in an ECG mode.

2. The measurement device of claim 1, wherein the first contact and the second contact correspond to a pair of differential signals of a measurement channel, and the third contact and the fourth contact correspond to a reference signal.

3. The measurement device of claim 1, wherein the operation circuit comprises:

a processor;

an EEG signal processing circuit, coupled to the processor;

an ECG signal processing circuit, coupled to the processor; and a switching circuit, for controlling the first contact, the second contact and the third contact to be coupled to the EEG signal processing circuit when the measurement device is in the EEG mode, and controlling the first contact, the second contact and the fourth contact to be coupled to the ECG signal processing circuit when the measurement device is in the ECG mode.

4. The measurement device of claim 3, wherein the operation circuit further comprises a signal transmission module, coupled to the processor, for transmitting a signal to an external electronic device after the signal is interpreted by the processor.

* * * * *